US011865307B2

(12) United States Patent
Schader et al.

(10) Patent No.: US 11,865,307 B2
(45) Date of Patent: Jan. 9, 2024

(54) MEDICAMENT INJECTION DEVICE (71) Applicant: Sanofi-Aventis Deutschland GMBH, Frankfurt am Main (DE)

(72) Inventors: Marc Schader, Frankfurt am Main (DE); Michael Helmer, Frankfurt am Main (DE); Peter Nober, Rommersheim (DE); Michael Varga, Donzdorf (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 17/566,155

(22) Filed: Dec. 30, 2021

(65) Prior Publication Data
US 2022/0118186 A1 Apr. 21, 2022

Related U.S. Application Data (63) Continuation of application No. 15/778,278, filed as application No. PCT/EP2016/078274 on Nov. 21, 2016, now Pat. No. 11,213,627.

(30) Foreign Application Priority Data

Nov. 27, 2015 (EP) .................................... 15196709

(51) Int. Cl.
*A61M 5/24* (2006.01)
*A61M 5/32* (2006.01)
(52) U.S. Cl.
CPC ........ *A61M 5/2466* (2013.01); *A61M 5/3202* (2013.01); *A61M 2005/2474* (2013.01)
(58) Field of Classification Search
CPC ........ A61M 2005/2474; A61M 5/2455; A61M 5/2466; A61M 5/3202
See application file for complete search history.

(56) References Cited

U.S. PATENT DOCUMENTS

| 3,916,893 | A | 11/1975 | De Felice |
| 5,250,037 | A | 10/1993 | Bitdinger |

(Continued)

FOREIGN PATENT DOCUMENTS

| CN | 102939123 | 2/2013 |
| CN | 103228306 | 7/2013 |

(Continued)

OTHER PUBLICATIONS

International Preliminary Report on Patentability in International Appln. No. PCT/EP2016/078274, dated May 29, 2018, 7 pages.

(Continued)

*Primary Examiner* — Shefali D Patel
(74) *Attorney, Agent, or Firm* — Fish & Richardson P.C.

(57) ABSTRACT

A medicament injection device comprising a main body arranged to receive a medicament cartridge; a needle carrier carrying a needle, wherein the needle carrier is axially movable with respect to the main body; and a rotatable cap at a distal end of the device, wherein the cap is removably coupled to the needle carrier, a releasable arrangement between the main body and the cap comprising a guide element and a slotted link, wherein the slotted link is arranged to cause the guide element to follow a predefined path at least partly in an axial direction during rotational movement of the cap, thereby causing the needle carrier to move axially towards a proximal end of the device as the cap is rotated up to a predefined point, wherein the main body comprises a medicament cartridge holder comprising the guide element depending therefrom for engagement with the cap.

29 Claims, 3 Drawing Sheets (56) References Cited

U.S. PATENT DOCUMENTS

| | | | |
|---|---|---|---|
| 11,213,627 | B2 | 1/2022 | Schader et al. |
| 2013/0035644 | A1 | 2/2013 | Giambattista et al. |
| 2014/0221916 | A1 | 8/2014 | Kramer et al. |
| 2014/0243741 | A1 | 8/2014 | Kaufmann et al. |
| 2015/0119815 | A1 | 4/2015 | Fuke et al. |
| 2015/0126925 | A1 | 5/2015 | Fuke et al. |
| 2018/0344934 | A1 | 12/2018 | Schader et al. |

FOREIGN PATENT DOCUMENTS

| | | |
|---|---|---|
| CN | 104470562 | 3/2015 |
| CN | 104487115 | 4/2015 |
| CN | 104884106 | 9/2015 |
| EP | 2724740 | 4/2014 |
| EP | 2923714 | 9/2015 |
| JP | H06-209996 | 8/1994 |
| JP | 2009-095392 | 5/2009 |
| JP | 2013-523314 | 6/2013 |
| JP | 2016-533214 | 10/2016 |
| JP | 2017-508546 | 3/2017 |
| WO | WO 1999/022790 | 5/1999 |
| WO | WO 2003/057289 | 7/2003 |
| WO | WO 2007/131013 | 11/2007 |
| WO | WO 2011/126439 | 10/2011 |
| WO | WO 2014/013594 | 1/2014 |
| WO | WO 2015/055592 | 4/2015 |
| WO | WO 2015/144870 | 10/2015 |

OTHER PUBLICATIONS

International Search Report and Written Opinion in International Appln. No. PCT/EP2016/078274, dated Feb. 20, 2017, 10 pages.

MEDICAMENT INJECTION DEVICE

CROSS REFERENCE TO RELATED APPLICATIONS

The present application is a continuation of U.S. patent application Ser. No. 15/778,278, filed on May 23, 2018, which is the national stage entry of International Patent Application No. PCT/EP2016/078274, filed on Nov. 21, 2016, and claims priority to Application No. EP 15196709.8, filed in on Nov. 27, 2015, the disclosures of which are incorporated herein by reference.

TECHNICAL FIELD

The present disclosure relates to a medicament injection device.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection.

SUMMARY

A first embodiment provides a medicament injection device comprising a main body arranged to receive a medicament cartridge; a needle carrier carrying a needle, wherein the needle carrier is axially movable with respect to the main body; and a rotatable cap at a distal end of the device, wherein the cap is removably coupled to the needle carrier, a releasable arrangement between the main body and the cap comprising a guide element and a slotted link, wherein the slotted link is arranged to cause the guide element to follow a predefined path at least partly in an axial direction during rotational movement of the cap, thereby causing the needle carrier to move axially towards a proximal end of the device as the cap is rotated up to a predefined point, wherein the main body comprises a medicament cartridge holder comprising the guide element depending therefrom for engagement with the cap.

The cap may comprise a tubular element, the outer surface of the tubular needle shielding element having the slotted link arranged thereon to receive the guide element.

The tubular element may contain a needle shield.

The slotted link may be configured to cause the cap to move axially in a distal axial direction when the cap is rotated beyond the predefined point.

The slotted link may comprise a portion that is relatively narrow in comparison to the remainder of the slotted link.

The slotted link may comprises an axially straight part.

The needle holder may be arranged to become fixed to the medicament cartridge after axial movement thereof in the proximal direction.

The needle holder may comprise a lip arranged to cooperate with a head of the medicament cartridge.

The needle holder may be dimensioned to form a frictional fit with the head of the medicament cartridge.

The medicament cartridge holder may contain a medicament cartridge having a penetrable barrier at a distal end thereof, and the axial movement of the needle carrier towards the proximal end may cause the needle to pierce the barrier of the medicament cartridge.

The medicament cartridge may contain a medicament.

The device may be an auto-injector.

A second embodiment provides a method of operating a medicament injection device having a rotatable cap, the method comprising: rotating the cap, thereby causing a releasable arrangement between the main body and the cap comprising a guide element and a slotted link to cooperate to cause a needle to move axially in a proximal direction and to penetrate a separable barrier of a medicament cartridge.

Further rotation of the cap may cause the cap to move axially in a distal direction.

BRIEF DESCRIPTION OF THE FIGURES

Exemplary embodiments of the present disclosure are described with reference to the accompanying drawings, in which.

DETAILED DESCRIPTION

Embodiments provide a mechanism for inserting the needle of an injection device such as an auto-injector or syringe into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in embodiments the user does not need to touch the needle during the steps of inserting the needle into the medicament cartridge and subsequently actuating the injection of the medicament.

Embodiments provide a mechanism whereby a needle holder holding a needle is automatically connected to a medicament cartridge in response to rotation of a device cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
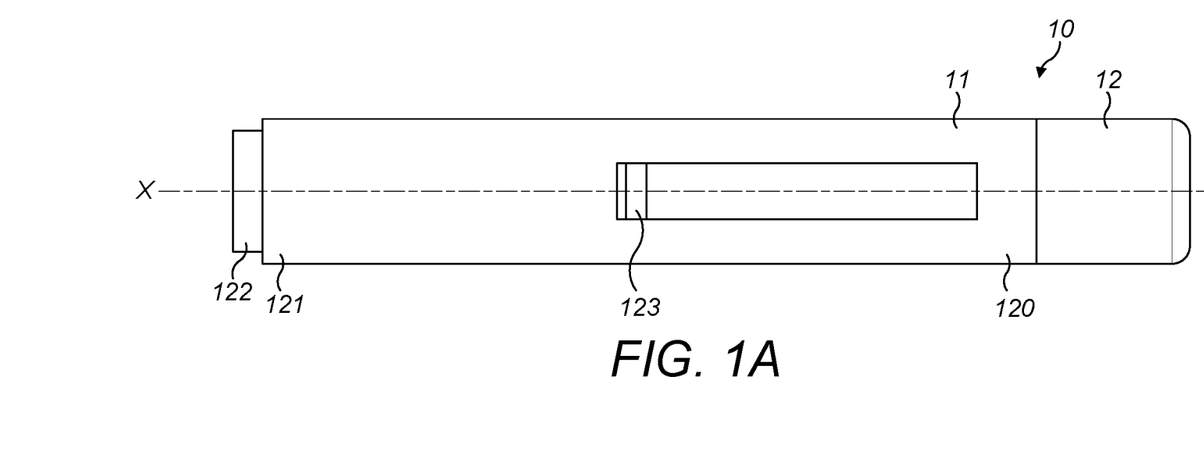
FIGS. 1A and 1B are side-on views of an auto-injector device according to embodiments of the disclosure.
Figure 1B:
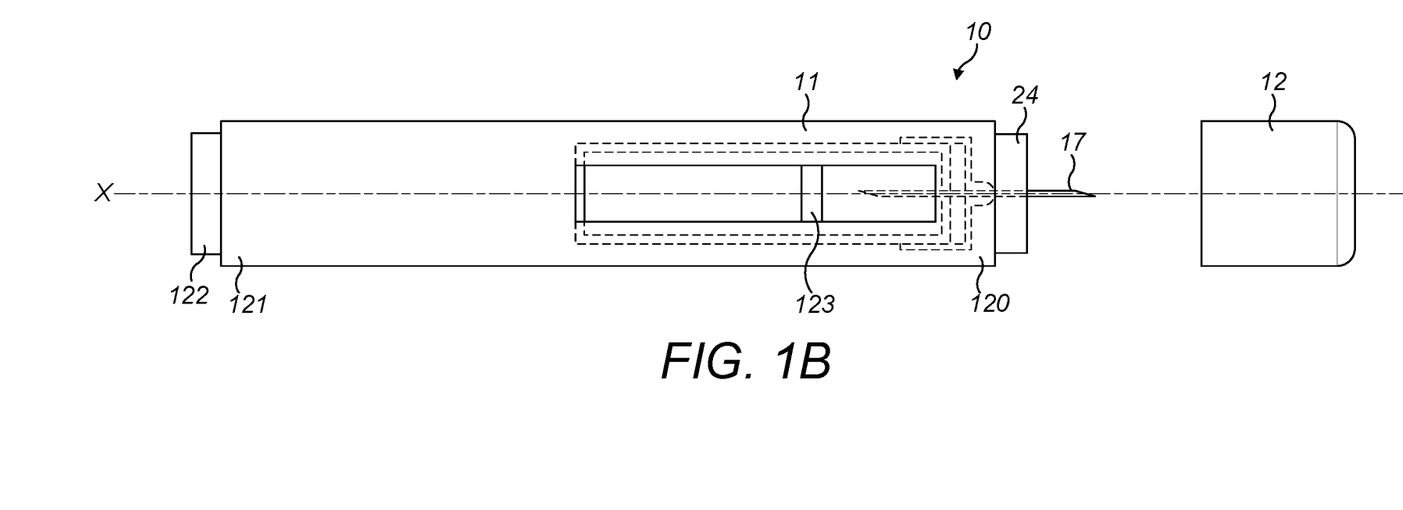

According to some embodiments of the present disclosure, an exemplary drug delivery device 10 is shown in FIGS. 1A & 1B. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 12 that can be detachably mounted to the main body 11. Typically a user must remove cap 12 from main body 11 before device 10 can be operated.

As shown, main body 11 is substantially cylindrical and has a substantially constant diameter along the longitudinal axis X. The main body 11 has a distal region 120 and a proximal region 121. The term "distal" refers to a location that is relatively closer to a site of injection, and the term "proximal" refers to a location that is relatively further away from the injection site.

Device 10 can also include a needle sleeve 24 coupled to main body 11 to permit movement of sleeve 24 relative to main body 11. For example, sleeve 24 can move in a longitudinal direction parallel to longitudinal axis X. Specifically, movement of sleeve 24 in a proximal direction can permit a needle 17 to extend from distal region 120 of main body 11.

Insertion of needle 17 can occur via several mechanisms. For example, needle 17 may be fixedly located relative to main body 11 and initially be located within an extended needle sleeve 24. Proximal movement of sleeve 24 by placing a distal end of sleeve 24 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 24.

Another form of insertion is "automated," whereby needle 17 moves relative to main body 11. Such insertion can be triggered by movement of sleeve 24 or by another form of activation, such as, for example, a button 122. As shown in FIGS. 1A & 1B, button 122 is located at a proximal end of main body 11. However, in other embodiments, button 122 could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within sleeve 24 or main body 11. Retraction can occur when sleeve 24 moves distally as a user removes device 10 from a patient's body. This can occur as needle 17 remains fixedly located relative to main body 11. Once a distal end of sleeve 24 has moved past a distal end of needle 17, and needle 17 is covered, sleeve 24 can be locked. Such locking can include locking any proximal movement of sleeve 24 relative to main body 11.

Another form of needle retraction can occur if needle 17 is moved relative to main body 11. Such movement can occur if the syringe within main body 11 is moved in a proximal direction relative to main body 11. This proximal movement can be achieved by using a retraction spring (not shown), located in distal region 120. A compressed retraction spring, when activated, can supply sufficient force to the syringe to move it in a proximal direction. Following sufficient retraction, any relative movement between needle 17 and main body 11 can be locked with a locking mechanism. In addition, button 122 or other components of device 10 can be locked as required.

Figure 2A:
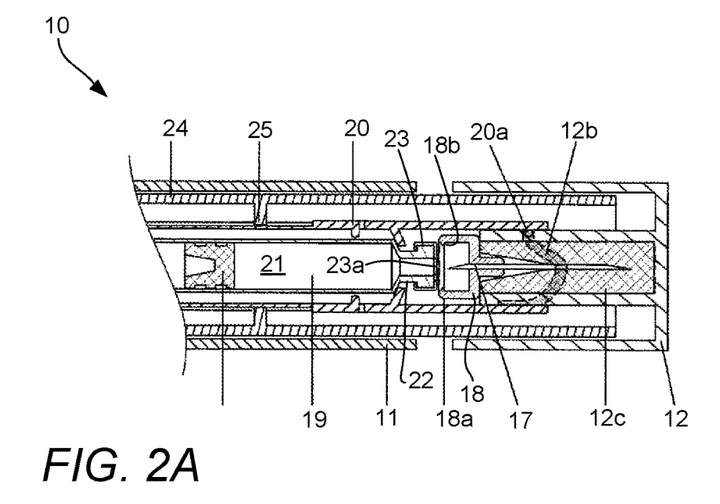
FIG. 2A is a side-on cross sectional schematic view of a device having a cap according to a first embodiment before the cap is rotated.

FIG. 2A shows a side-on cross-section of an auto-injector device 10 according to a first embodiment of the disclosure. The device 10 comprises a generally cylindrical main body 11 and a generally cylindrical cap 12.

The device 10 also comprises a tubular needle sleeve 24 that fits inside the main body 11 and is arranged to slide axially with respect to the main body 11. The needle sleeve 24 is a protective sleeve that prevents unwanted exposure of the needle 17. The needle sleeve 24 has a similar shape to the main body and is hollow and generally cylindrical.

The cap 12 has an end wall and a curved side wall and a tubular wall 12a extending from the end wall containing a needle shield 12c. The needle shield 12c protects a distal end of the needle 17 during storage. The needle shield 12c acts to seal the needle 17. There may be provided a press fit, form fit or adhesive bond between the needle shield 12c and the tubular wall 12a.

The needle shield material can be an elastomer like known needle shields for syringes for auto injectors. The needle shield can also be made out of thermoplastic elastomer (TPE) which may be 2K injection moulded into the cap 12.

The needle shield is fixed to the cap regarding movement in an axial direction, so that the needle shield 12c is removed when the cap is removed.

The cap 12 fits over the needle sleeve 24. The cap 12 is movable axially with respect to the main body 11.

The device 10 comprises a cartridge 19 which is held in place by a cartridge holder 20. The cartridge holder 20 and cartridge 19 are connected and fixed relative to the main body 11 of the device 10. The cartridge 19 may be provided to a user separately to the device 10. The user may insert the cartridge 19 into the device 10.

The device 10 comprises a needle 17 which is held towards the proximal end thereof by a needle holder 18. The distal end of the needle 17 is covered by the tubular member 12a of the cap 12. The needle holder 18 which holds the needle 17 is axially movable relative to the main body 11 and the cartridge 19.

The cartridge 19 has a cartridge body 21, a neck 22 and a head 23. The head 23 is wider than the neck 22, thereby forming a flanged end. The neck 22 and head 23 contain a passage allowing medicament to pass therethrough as well as to receive the needle 17 once inserted. The head 23 is provided with a penetrable barrier such as a septum 23a to close off the passage and to seal the contents of the medicament cartridge 19. The cartridge body 21, neck 22 and head 23 may be generally cylindrical in shape. However, alternative shapes may be employed. The cup-shaped portion 18a is shaped to engage with the head 23 of the cartridge 19.

The cartridge holder 20 is generally tubular and is coaxial with respect to the main body 11. The main wall of the cartridge holder 20 extends around the body 21 of the cartridge 19 and extends towards the distal end of the device 10 so that it surrounds the head 23 of the cartridge 19, the needle holder 18 and a proximal end portion of the tubular member 12a of the cap 12. The cartridge holder 20 has a diameter greater than that of the cartridge 19 and needle holder 18. The cartridge holder 20 has ribs 25 extending inwardly from the main wall to support the cartridge 19 along the length of the cartridge 19. Alternatively, the cartridge holder 20 has a diameter approximately equal to that of the cartridge 19 so that a frictional fit is provided between the cartridge 19 and the cartridge holder 20 so that the ribs are not necessary. The cartridge holder 20 has a diameter approximately equal to that of the tubular member 12a so that a frictional fit is achieved when the cap 12 is attached to the rest of the device 10, as shown in FIG. 2A.

The cartridge holder 20 has a guide element 20a such as a pin extending from the inner surface of the main wall of the cartridge holder 20. The guide element 20a engages with a slotted link 12b which is a groove provided in the outer surface of the tubular member 12a of the cap 12. The slotted link 12b defines a path followed by the guide element 20a as the cap 12 is rotated by the user and as the cap is pulled away from the main body.

Figure 2B:
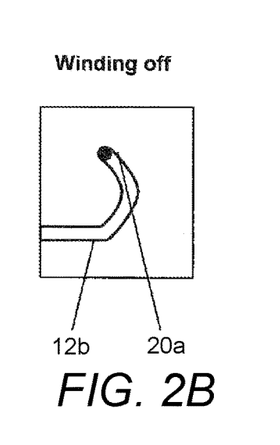
FIG. 2B is a representation of the engagement of a guide element with a slotted link in the device shown in FIG. 2A.

FIG. 2B is a projection of the path defined by the slotted link 12b onto a two-dimensional surface. The slotted link 12b is generally hooked shaped in this projection. The curved portion shown in FIG. 2B defines the path taken by the guide element 20a as the user rotates the cap 12. The curved path defined by the slotted link varies axially as well as running circumferentially around the tubular member 12a. Therefore movement of the fixed guide element 20a along the path defined by the slotted link results in axial movement of the cap 12 as the cap 12 is rotated relative to the main body 11.

The straight portion of the slotted link 12b defines the path taken by the guide element 20a as the user pulls the cap 12 from the main body 11 subsequent to rotation of the cap 12 and the attachment of the needle holder 18 to the medicament cartridge 19. The slotted link 12b prevents detachment of the cap 12 before the cap has been rotated sufficiently to ensure attachment of the needle holder 18 to the medicament cartridge 19.

The needle holder 18 which holds the needle 17 is axially movable relative to the main body 11 and the cartridge 19. The needle holder has a generally cup-shaped portion 18a and a passage through which the needle 17 passes. The cup-shaped portion 18a is shaped to engage with the head 23 of the cartridge 19. The cup-shaped portion 18a comprises a lip 18b which serves to clip onto the head 23 to prevent detachment of the needle holder 18 from the cartridge 19 subsequent to attachment of the needle holder 18 to the cartridge 19. Both ends of the needle 17 are sharp. The proximal end is sufficiently sharp to enable the needle 17 to penetrate the septum 23a of the medicament cartridge 19. The distal end of the needle 17 is sufficiently sharp to allow the needle to penetrate the patient's skin.

Figure 3A:
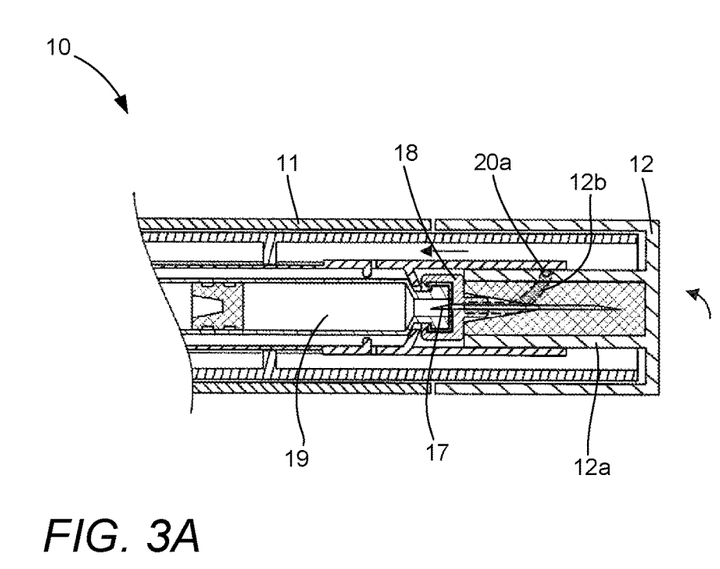
FIG. 3A is a side-on cross sectional schematic view of the device of the first embodiment as the cap is rotated.

FIG. 3A shows the device 10 as the user rotates the cap 12. The guide element 20a moves along a curved portion of the path defined by the slotted link 12b. In FIG. 3, the guide element 20a is located in the part of the slotted link 12b furthest away from the proximal end of the tubular member 12a. Since the position of the guide element 20a is fixed axially with respect to the main body 11 and medicament cartridge 19 and cap 12 are axially movable with respect to the main body 11 and medicament cartridge 19, the rotation of the cap 12 from the position shown in FIGS. 2A and 2B leads to an axial movement of the cap 12 towards the medicament cartridge 19. The tubular member 12a abuts the needle holder 18 thereby causing axial movement of the needle holder towards the medicament cartridge 19.

As shown in FIG. 3A, the needle 17 pierces the septum 23a of the medicament cartridge 19, thereby establishing a passage for the medicament to flow from the medicament cartridge 19 to the distal end of the needle 17.

After moving axially towards the medicament cartridge, the cup-shaped part 18a of the needle holder 18 fits over the head 23 of the medicament cartridge 19. Moreover, the lip 18b extending around the cup-shaped part 18a of the needle holder further serves to fix the needle holder 18 to the medicament cartridge 19. The lip 18b has a tapered leading edge to allow the cup shaped part to fit over the head 23.

In alternative embodiments, no lip is provided. The diameter of the cup shaped part 18a and the diameter of the head 23 of the medicament cartridge 19 can be arranged to ensure a close frictional fit between the needle holder 18 and the medicament cartridge 19.

However, once the needle holder 18 is fitted to the medicament cartridge 19, axial movement of the needle holder away, and separation from, the medicament cartridge 19 is prevented by the lip or the frictional fit.

Figure 3B:
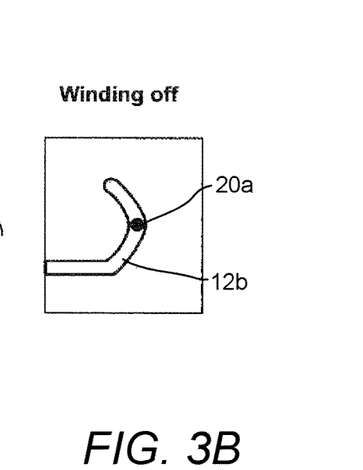
FIG. 3B is a representation of the engagement of the guide element with the slotted link in the device shown in FIG. 3A.

As the cap 12 is rotated beyond the position shown in FIG. 3A, the guide element 20a is guided along the curved portion of the slotted link 12b between the guide element 20a position shown in FIG. 3B and the axially straight portion of the path. Because of the direction of the curve of the slotted link, rotation of the cap at this stage causes the cap 12 to move axially away from the needle holder 18 and the medicament cartridge 19.

Figure 4A:
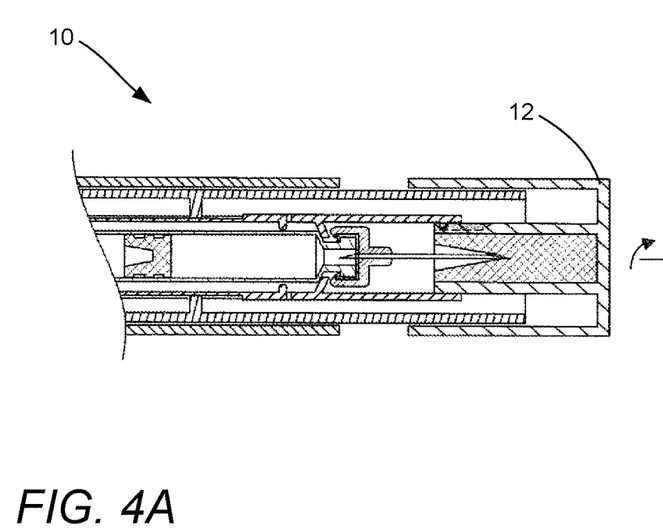
FIG. 4A is a side-on cross sectional schematic view of the device of the first embodiment as the cap is being removed.
Figure 4B:
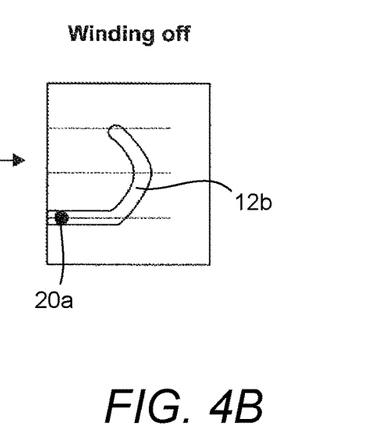
FIG. 4B is a representation of the engagement of the guide element with the slotted link in the device shown in FIG. 4A.

FIGS. 4A and 4B show the device 10 as the cap 12 is removed. The guide element 20a reaches the axially straight portion of the slotted link 12b. The cap 12 can no longer be rotated because of the axial direction of the slotted link 12b. The user pulls the cap 12 away from the main body 11 in the distal direction.

Once the cap 12 has been removed, the user may commence the injection. The distal end of the device 10 is held against the patient's injection site and the device actuated.

Figure 5:
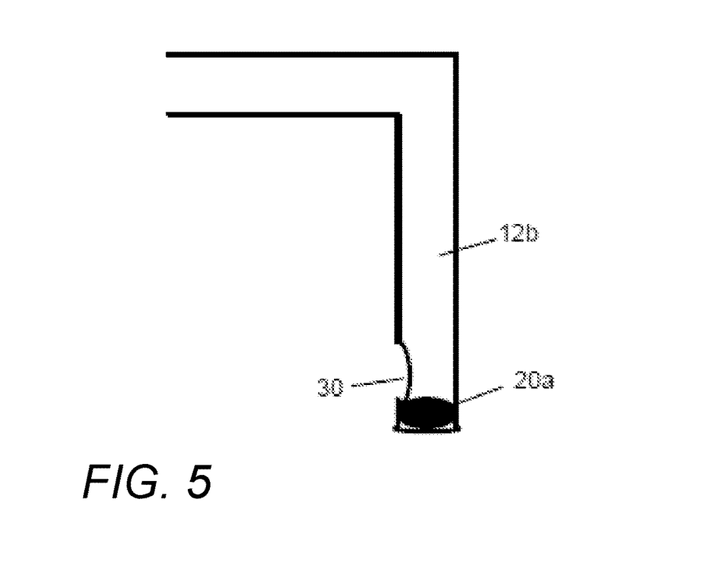
FIG. 5 shows a narrowing of a slotted link.

In some embodiments, as shown in FIG. 5, the slotted link may 12b may have a narrowed portion 30 that is narrower than the rest of the slotted link 12b. This helps to prevent accidental rotation of the cap 12 so that the needle 17 is not inserted into the cartridge 19 prematurely.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A method of operating a medicament injection device having a rotatable cap, the method comprising:
   rotating the rotatable cap, thereby causing a releasable arrangement between a main body and the rotatable cap to cooperate to cause the rotatable cap to move axially in a proximal direction during rotational movement of the rotatable cap, thereby causing a needle holder to become attached to a medicament cartridge and causing a needle of the needle holder to move axially in the proximal direction so as to penetrate a separable barrier of the medicament cartridge, as the rotatable cap is rotated up to a predefined point, wherein the releasable arrangement comprises a guide element and a slotted link; and
   rotating the rotatable cap beyond the predefined point, thereby causing the releasable arrangement to cooperate to cause the rotatable cap to move axially in a distal direction during the rotational movement of the rotatable cap beyond the predefined point.

2. The method of claim 1, wherein the slotted link comprises a hook-shaped curved portion and a straight portion, wherein the straight portion is configured so as to prevent further rotation of the cap as the cap is removed from the device.

3. The method of claim 1, wherein the main body comprises a medicament cartridge holder arranged within the main body of the medicament injection device.

4. The method of claim 3, wherein the guide element depends from the medicament cartridge holder for engagement with the rotatable cap.

5. The method of claim 3, wherein the medicament cartridge holder comprises a main wall extending around the cartridge and extends towards a distal end of the device so that the main wall of the cartridge holder surrounds a head of the cartridge.

6. The method of claim 1, wherein the rotatable cap comprises a tubular element, an outer surface of the tubular element having the slotted link arranged thereon to receive the guide element.

7. The method of claim 1, wherein the medicament cartridge comprises a head and wherein the needle holder comprises a lip arranged to clip onto the head to prevent detachment of the needle holder from the medicament cartridge subsequent to the attachment of the needle holder to the cartridge.

8. The method of claim 1, wherein the needle holder is dimensioned to form a frictional fit with a head of the medicament cartridge to prevent detachment of the needle holder from the medicament cartridge.

9. The method of claim 1, wherein the separable barrier is located at a distal-most end of the medicament cartridge.

10. The method of claim 1, wherein the medicament cartridge comprises a head and wherein the needle holder comprises a cup-shaped portion shaped to engage with the head of the cartridge.

11. A method of operating a medicament injection device having a rotatable cap, the method comprising:
    rotating the rotatable cap, thereby causing a releasable arrangement between a main body of the medicament injection device and the rotatable cap to cooperate to cause the rotatable cap to move axially in a proximal direction during rotational movement of the rotatable cap, thereby causing a needle holder to become attached to a medicament cartridge arranged within the main body of the medicament injection device and causing a needle of the needle holder to move axially in the proximal direction so as to penetrate a separable barrier of the medicament cartridge, as the rotatable cap is rotated up to a predefined point, wherein the releasable arrangement comprises a guide element and a slotted link; and
    rotating the rotatable cap beyond the predefined point, thereby causing the releasable arrangement to cooperate to cause the rotatable cap to move axially in a distal direction during the rotational movement of the rotatable cap beyond the predefined point.

12. The method of claim 11, wherein the slotted link comprises a hook-shaped curved portion and a straight portion, wherein the straight portion is configured so as to prevent further rotation of the cap as the cap is removed from the device.

13. The method of claim 11, wherein the main body comprises a medicament cartridge holder arranged within the main body of the medicament injection device.

14. The method of claim 13, wherein the guide element depends from the medicament cartridge holder for engagement with the rotatable cap.

15. The method of claim 13, wherein the cartridge holder comprises a main wall extending around the cartridge and extends towards a distal end of the device so that the main wall of the cartridge holder surrounds a head of the cartridge.

16. The method of claim 11, wherein the rotatable cap comprises a tubular element, an outer surface of the tubular element having the slotted link arranged thereon to receive the guide element.

17. The method of claim 11, wherein the medicament cartridge comprises a head and wherein the needle holder comprises a lip arranged to clip onto the head to prevent detachment of the needle holder from the cartridge subsequent to the attachment of the needle holder to the cartridge.

18. The method of claim 11, wherein the medicament cartridge comprises a head and wherein the needle holder is dimensioned to form a frictional fit with the head of the medicament cartridge.

19. The method of claim 11, wherein the separable barrier is located at a distal-most end of the medicament cartridge.

20. The method of claim 11, wherein the medicament cartridge comprises a head and wherein the needle holder comprises a cup-shaped portion shaped to engage with the head of the cartridge.

21. A method of operating a medicament injection device having a rotatable cap, the method comprising:
rotating the rotatable cap, thereby causing a releasable arrangement between a main body of the injection device and the rotatable cap to cooperate to cause the rotatable cap to move axially in a proximal direction during rotational movement of the rotatable cap, thereby causing a needle holder to become attached to a medicament cartridge held by a medicament cartridge holder arranged within the main body of the medicament injection device and causing a needle of the needle holder to move axially in the proximal direction so as to penetrate a separable barrier of the medicament cartridge, as the rotatable cap is rotated up to a predefined point, wherein the releasable arrangement comprises a guide element and a slotted link; and
rotating the rotatable cap beyond the predefined point, thereby causing the releasable arrangement to cooperate to cause the rotatable cap to move axially in a distal direction during the rotational movement of the rotatable cap beyond the predefined point.

22. The method of claim 21, wherein the slotted link comprises a hook-shaped curved portion and a straight portion, wherein the straight portion is configured so as to prevent further rotation of the cap as the cap is removed from the device.

23. The method of claim 21, wherein the guide element depends from the medicament cartridge holder for engagement with the rotatable cap.

24. The method of claim 21, wherein the cartridge holder comprises a main wall extending around the cartridge and extends towards a distal end of the device so that the main wall of the cartridge holder surrounds a head of the cartridge.

25. The method of claim 21, wherein the rotatable cap comprises a tubular element, an outer surface of the tubular element having the slotted link arranged thereon to receive the guide element.

26. The method of claim 21, wherein the medicament cartridge comprises a head and wherein the needle holder comprises a lip arranged to clip onto the head to prevent detachment of the needle holder from the cartridge subsequent to the attachment of the needle holder to the cartridge.

27. The method of claim 21, wherein the medicament cartridge comprises a head and wherein the needle holder is dimensioned to form a frictional fit with the head of the medicament cartridge.

28. The method of claim 21, wherein the separable barrier is located at a distal-most end of the medicament cartridge.

29. The method of claim 21, wherein the medicament cartridge comprises a head and wherein the needle holder comprises a cup-shaped portion shaped to engage with the head of the cartridge.

* * * * *

UNITED STATES PATENT AND TRADEMARK OFFICE
CERTIFICATE OF CORRECTION

| | | |
|---|---|---|
| PATENT NO. | : 11,865,307 B2 | Page 1 of 1 |
| APPLICATION NO. | : 17/566155 | |
| DATED | : January 9, 2024 | |
| INVENTOR(S) | : Marc Schader et al. | |

It is certified that error appears in the above-identified patent and that said Letters Patent is hereby corrected as shown below:

In the Specification

In Column 1, Line 11 (approx.), delete "in on" and insert -- on --

Signed and Sealed this
First Day of October, 2024

Katherine Kelly Vidal
*Director of the United States Patent and Trademark Office*